United States Patent
Murphy et al.

[11] Patent Number: 5,233,713
[45] Date of Patent: Aug. 10, 1993

[54] HEAD HOLDER FOR NUCLEAR IMAGING

[75] Inventors: Lawrence E. Murphy, Shorewood; Richard A. Valiga, Waukesha, both of Wis.

[73] Assignee: General Electric Company, Milwaukee, Wis.

[21] Appl. No.: 857,697

[22] Filed: Mar. 25, 1992

Related U.S. Application Data

[63] Continuation of Ser. No. 676,148, Mar. 27, 1991, abandoned.

[51] Int. Cl.⁵ .............................................. A61G 13/00
[52] U.S. Cl. .................................. 5/636; 378/209; 5/601; 5/622; 606/130
[58] Field of Search ............... 269/322, 323, 325, 326, 269/327, 328; 5/434–435, 436, 437, 636, 601, 622; 378/208, 209; 606/130

[56] References Cited

U.S. PATENT DOCUMENTS

| | | | |
|---|---|---|---|
| 325,551 | 9/1885 | Lukens | 269/328 |
| 600,395 | 3/1898 | Adams | 269/328 |
| 4,061,324 | 12/1977 | Kvaerena et al. | 269/325 |
| 4,266,760 | 10/1981 | Matsui et al. | 269/328 |
| 4,515,354 | 5/1985 | Chandler et al. | 269/289 R |
| 4,698,837 | 10/1987 | Van Steenberg | 269/328 |
| 4,841,965 | 6/1989 | Jacobs | 269/328 |

OTHER PUBLICATIONS

General Electric Company Product Data Sheet H2504AE, undated.

*Primary Examiner*—Bruce M. Kisliuk
*Assistant Examiner*—Eileen P. Morgan
*Attorney, Agent, or Firm*—Quarles & Brady

[57] ABSTRACT

A head holder device for use in conjunction with an imaging table wherein the head holder has a shape to comfortably receive the head of a person and is open at the bottom for improved imaging. A bracket member provides a first pivotal connection to the head holder at one end. There is a second pivotal connection for attachment to either an imaging table or a mounting panel. In a preferred embodiment, one of the pivotal connections also provides for length adjustment.

8 Claims, 3 Drawing Sheets

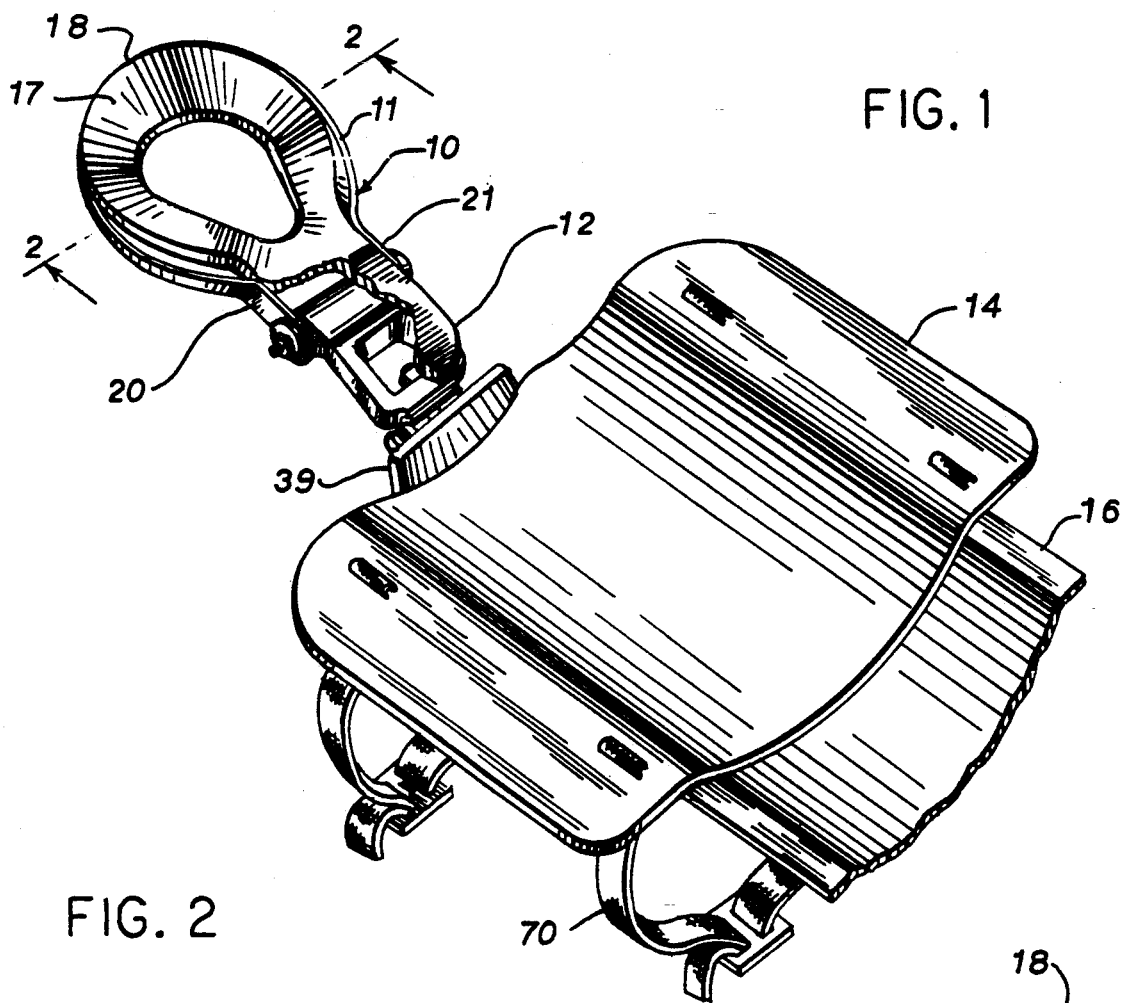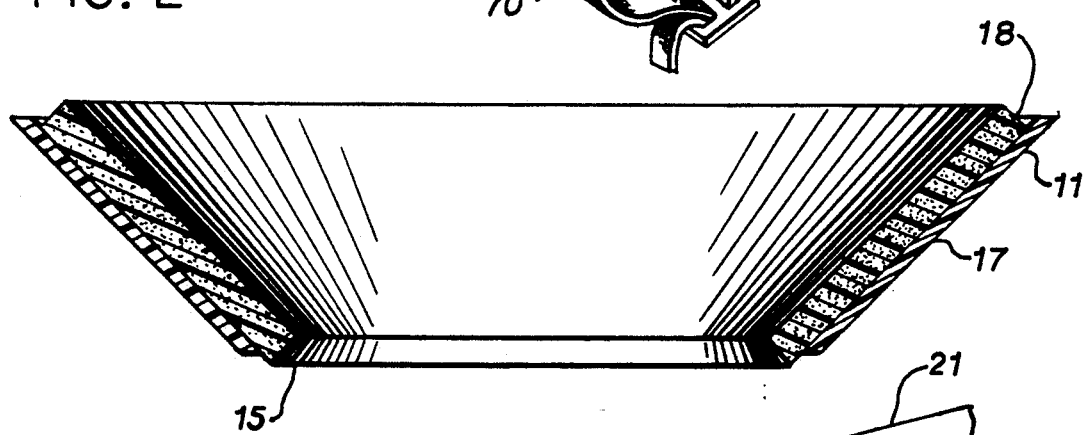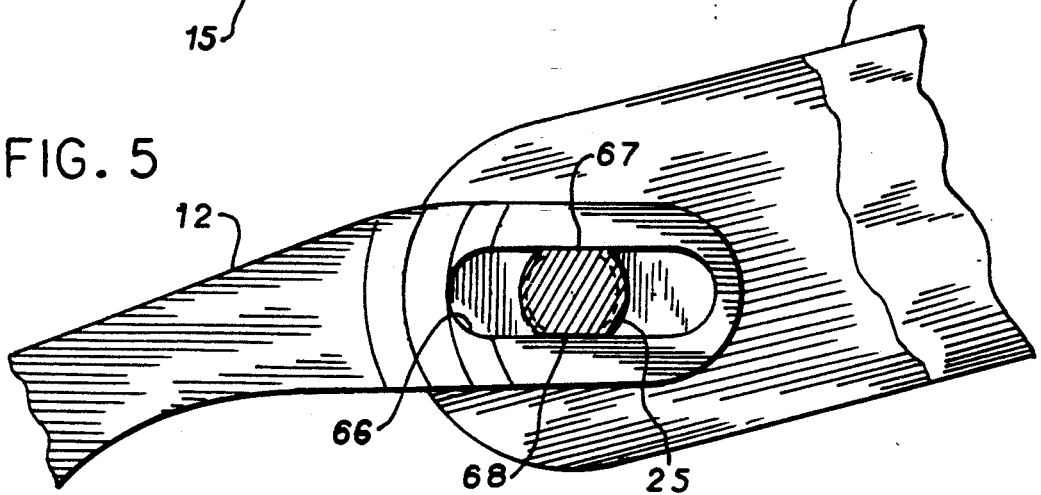

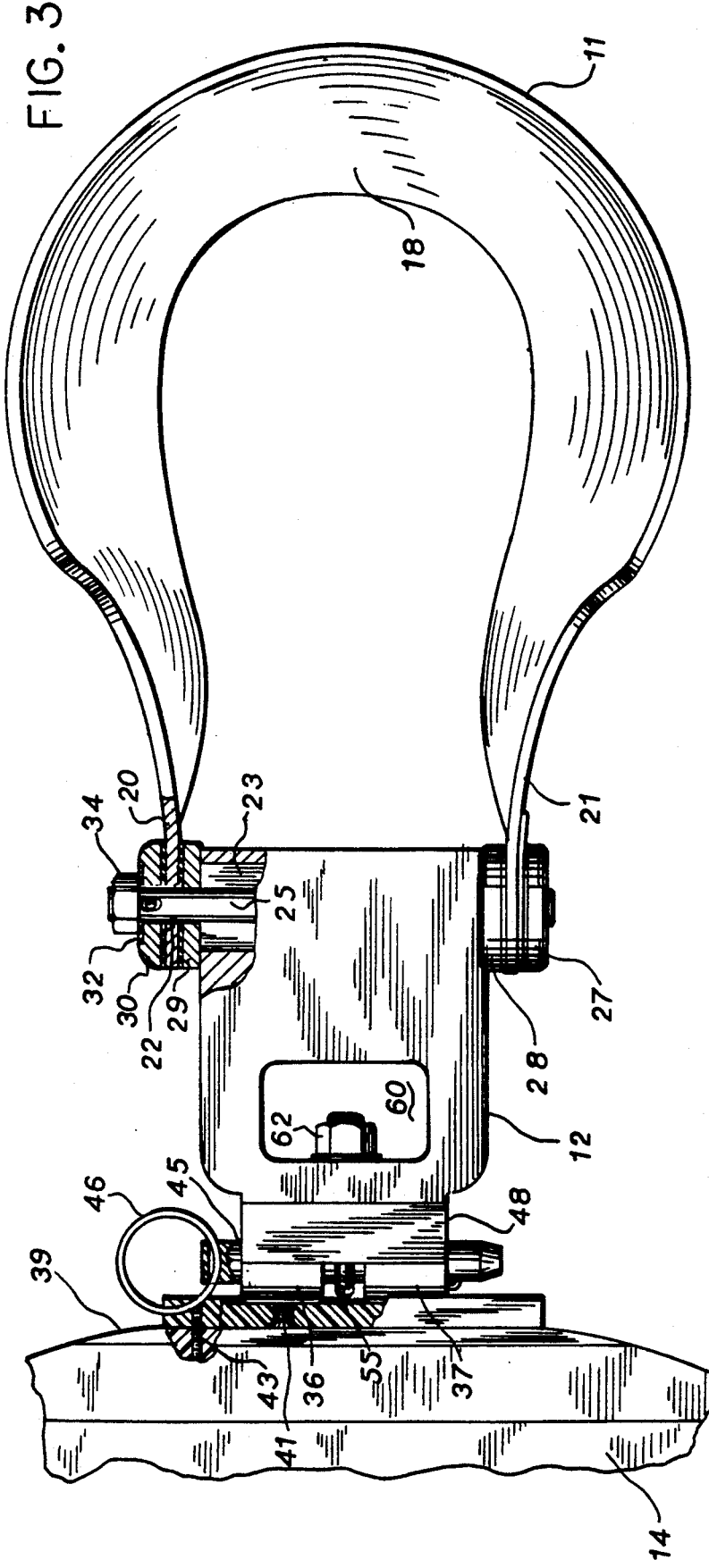

HEAD HOLDER FOR NUCLEAR IMAGING

This application is a continuation of application Ser. No. 07/676,148, filed Mar. 27, 1991, now abandoned.

BACKGROUND OF THE INVENTION

This invention relates to a head holder used in conjunction with diagnostic procedures. More particularly, it relates to an improved articulating head holder for use in nuclear imaging wherein the head holder effects a reduction in interference with the holder yet allows for multiple adjustments.

Currently there are available head holders for use with nuclear imaging. These are basically composed of acrylic sheet material which is formed into a "U" shape for supporting the head. One pivotal adjustment is provided to position the head.

Prior head holders interfere with imaging techniques particularly where tomographic imaging is involved. They also do not afford multiple position adjustments such as pivotal and length adjustment. Further, they are not comfortable to the patent and afford only limited operator interface.

SUMMARY OF THE INVENTION

The invention provides a head holder for use in conjunction with an imaging table. There is a head holder member with a bracket member connected to the head holder member by a first pivotal connection at one end. There is a second pivotal connection attaching the bracket member at an opposing end of the bracket member opposite to the first pivotal connection and for attachment to a support means. Both pivotal connections are disposed parallel to each other.

In a preferred manner, the head holder includes position indicator means operatively associated with the pivotal connections.

In another preferred embodiment, the head holder includes an upwardly and outwardly extending curved wall for supporting a body head with an opening disposed through the holder adjacent the bottom of the wall with the wall presenting a substantially conical configuration.

In one aspect there is an insert member for insertion in the head holder member with the insert member having a head holder portion having an upwardly extending wall complementary to the head holder wall with an opening disposed therethrough for placement within the head holder wall. The wall of the insert member is composed of a substantially resilient material.

In yet another embodiment there is a mounting panel for connection to an imaging table with the bracket member connected to the mounting panel by an additional bracket.

It is, therefore, an object of the present invention to provide an improved head holder for an imaging apparatus.

It is another object of this invention to provide an articulated head holder of the foregoing type which is capable of multiple adjustments.

It is yet another object of this invention to provide a head holder of the foregoing type which results in improved tomography imaging.

It is still another object of the invention to provide a head holder of the foregoing type which can be operated in conjunction with additional equipment to afford additional versatility.

It is yet another object of this invention to provide a head holder of the foregoing type which lends itself to use with a replaceable insert for sanitary and additional comfort purposes.

The foregoing and other objects and advantages of the invention will appear from the following description. In the description, reference is made to the accompanying drawing which forms a part thereof, and in which there is shown by way of illustration preferred embodiments of the invention. Such embodiments do not necessarily represent the full scope of the invention, however, and reference is therefore made to the claims herein for interpreting the scope of the invention.

BRIEF DESCRIPTION OF THE DRAWINGS

A better understanding of the present head holder device will be had by reference to the drawings wherein:

FIG. 1 is a top perspective view showing the head holder device in connection with a mounting panel and an examining table.

FIG. 2 is a view in vertical section taken along line 2—2 of FIG. 1.

FIG. 3 is a top plan view of the head holder as shown in FIG. 1 with portions broken away.

FIG. 4 is a view in side elevation of the head holder as shown in FIG. 3 with portions shown in section.

FIG. 5 is a partial enlarged view showing an interconnection between the head holder and a bracket member.

DESCRIPTION OF THE EMBODIMENTS

Figure 6:
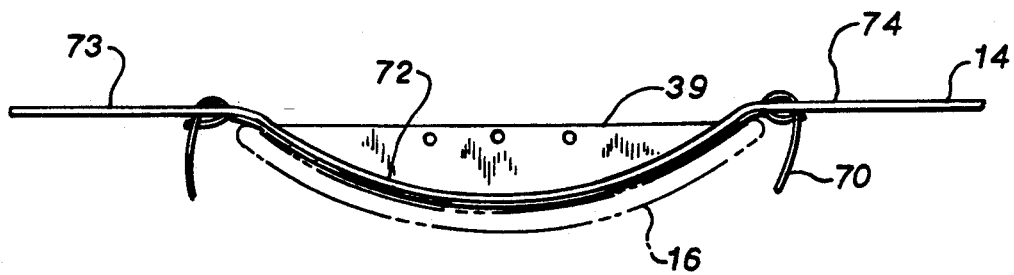
FIG. 6 is an end view illustrating a slide member which is connected to the head holder with the slide member positioned over the examining table.

Proceeding to a detailed description of the present invention and as best seen in FIG. 1, the head holder device generally 10 includes a head holder member 11 connected to a bracket member 12 which in turn is connected to a mounting panel 14 for engagement over an examining table 16. The head holder 11 is preferably composed of a carbon fiber which is formed in an open conical shape. This is best seen in conjunction with FIG. 2 where there is a foam insert member 18 having a head portion 13 of substantially the same shape as well as a tongue portion 19 for covering the bracket member 12. This gives the insert member 18 a substantially tear drop configuration when viewed in a plane substantially transverse to the conical configuration. It should also be pointed out that the head holder member 11 and insert 18 are open at the bottom as indicated by the numeral 15.

The head holder member 11 is pivotally mounted to the bracket 12. As best seen in FIG. 3, this is effected by the shaft 25 passing through the opening 22 of the flanges 20 and 21 as well as through the opening 23 in the bracket 12. Adjustable attachment is afforded by the spacers 28, 29 and 30. A rounded nut 27 is internally threaded to the shaft 25 at one end and at the opposing end with the usual hex nut 34 secured to the post 25 as well as the washer 32.

Referring specifically to FIGS. 3 and 4, the bracket 12 is shown pivotally attached to the bracket 39 which is fastened to the mounting panel 14. Suitable screws 43 provide the attachment. Connected to the bracket 39 such as by the screw 41 are two sleeves 36 and 37. These sleeves are internally knurled to receive the pin 45 in a frictional manner. It has the pull ring 46 at one end for easy removal. There is a block 48 which has an arcuate surface 50 extending over the sleeves 36 and 37. The block 48 has an internal passage 52 which is substantially "Y" shaped to receive the eye 55 of the bolt 54 as well as the shank 56 with pin 45 passing through the eye 55. The bracket 12 also has an aligned passage 58 for the bolt shank 56 to pass therethrough. The shank end 56 of the bolt 54 is secured by the nut 62 and the washer 63 positioned in the opening 60 to provide accessibility for adjustment. It should be noted particularly in conjunction with FIG. 4 that an allen screw 64 extends through the sleeve 36 so as to nonrotably mount the pin 45 in the sleeves 36 and 37.

FIG. 5 illustrates the pivotal connection between the head holder member flanges 21 and 22 and the bracket 12 by the shaft 25. As seen therein, the shaft 25 has the flat portions 67 and 68 so as to provide a nonrotable mounting in the elongated slot 66 of the bracket 12 while permitting pivoting of the head holder member 11. The elongated slot 66 also affords longitudinal adjustment of the head holder member 11.

FIG. 6 illustrates the relationship of the mounting panel 14 to the table 16. It will be seen that the mounting panel 14 has a central concave portion 72 and lateral flat portions 73 and 74 for supporting a patient's arms. Two straps 70 are provided to secure the mounting panel 14 to the table 16.

Figure 7:
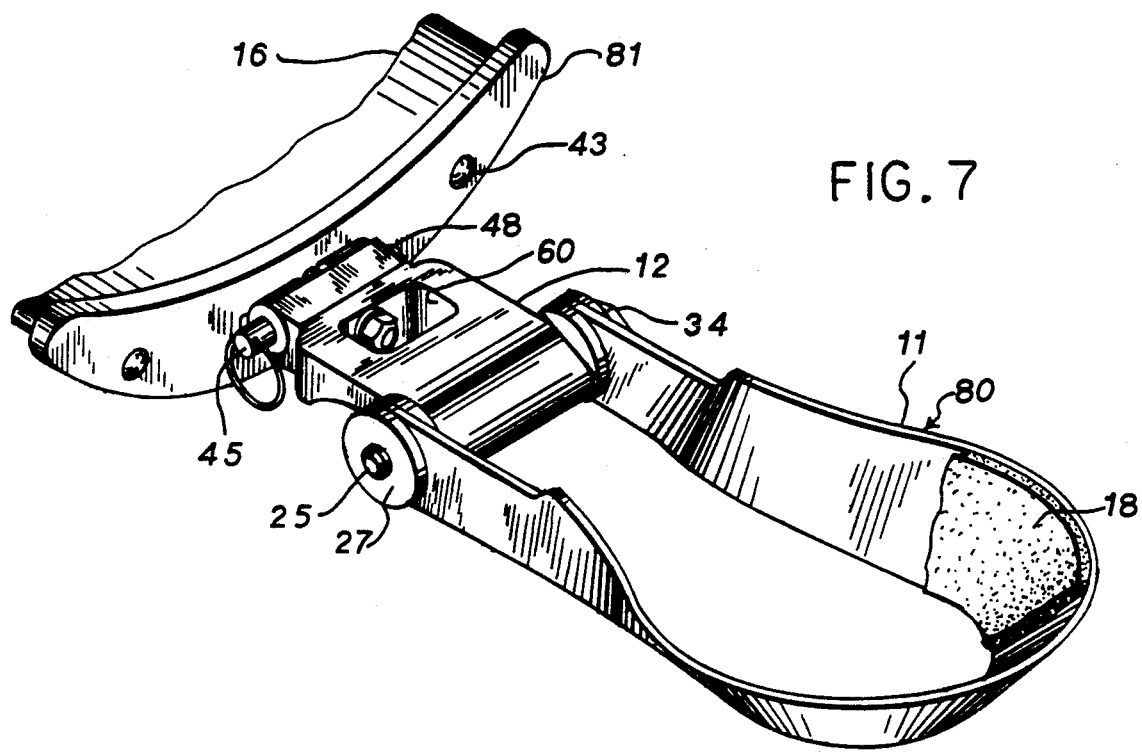
FIG. 7 is a top perspective view of an alternative embodiment.

Turning to FIG. 7, there is shown an alternative embodiment generally 80 wherein the same components as previously described have the same numbers. The difference between this embodiment 80 and embodiment 10 is the mounting of the head holder member 11 and the bracket 12 directly to the examining table 16 such as by means of the bracket 81. This would be provided in the instance where it is not desired to utilize the mounting panel 14. Screws 43 provide the attachment.

Figure 8:
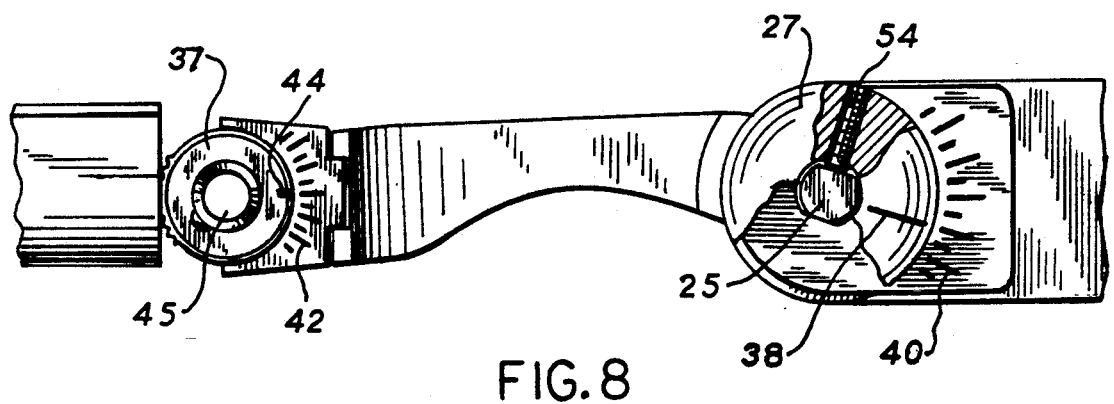
FIG. 8 is an enlarged partial view in side elevation illustrating the indicia for positioning the head holder and bracket members.

In FIG. 8 there is illustrated indicia 40 and 42 in conjunction with the parallel pivot connections afforded by pin 45 and shaft 25. There are indicators 44 and 38 on sleeve 37 and nut 27, respectively for reference purposes to indicate angular adjustment.

Important features of the head holder devices 10 and 80 are: First, the open conical form of the head holder 11 and insert 18 eliminates interference with imaging as well as improving patient comfort by providing the sloping curved and conical wall 17; Second, two angular adjustments for the head holder which are provided by the parallel shaft 25 and the pin 45; Third, a length adjustment for the head holder as provided by the elongated slot 66; Fourth, the adaptability of being able to attach the head holder device to a mounting panel or directly to an examining table; and Fifth, the accessibility of adjustment as afforded by the opening 60 and access to nuts 27 and 34.

While the head holder has been shown in conjunction with two parallel adjustment features, it should be appreciated that the improved characteristics of imaging and comfort can be accomplished without these. In the same manner, the adjustment features can be accomplished without the specific contour and opening of the head holder. While certain adjusting nuts such as 27, 34 and 62 have been illustrated, it is obvious that these could be replaced with other fastening devices such as spring biased fasteners or ratchet mechanisms.

The insert 18 is stated as composed of a foam material. Polyurethane having a four pound density is the preferred foam material. However, any commonly used resilient materials could be used such as a polyester open cell foam.

We claim:

1. A head holder device for use with an imaging table comprising:
    a head holder member defined by an upwardly and outwardly extending curved wall for supporting a body head with an opening disposed through said holder adjacent said wall, said wall defining a tapering side wall on all portions of said side wall, and with said opening presenting a substantially conical configuration in one plane and in a plane transverse thereto defining an enlarged section for said opening and a tapering narrow section, said curved wall being composed of a carbon fiber material;
    a bracket member, said bracket member connected to said head holder member by a first pivotal connection at one end;
    a second pivotal connection attached to said bracket member at an opposing end of said bracket member opposite to said first pivotal connection and for attachment to a support means with both said pivotal connections being disposed parallel to each other; and
    an insert member composed of a resilient material for insertion in said head holder member, said insert member having a head holder portion having substantially the same configuration as said head holder with an opening disposed through said insert member and complementary to said opening in said head holder, said insert member having a side wall for covering substantially all portions of said side wall of said head holder member.

2. The head holder device of claim 1 further including head holder member position indicator means operatively associated with said pivotal connections and said head holder member and said bracket member.

3. The head holder device of claim 1 wherein said first pivotal connection is defined by elongated slots in said bracket member.

4. The head holder device of claim 1 further including an extending portion connected to said insert member for placement over said bracket member.

5. A head holder deice of claim 1 further including a mountain panel for connection to an imaging table with said bracket member a connected to said mounting panel.

6. A head holder member for use with an imaging table comprising:
    a head holder member having an upwardly extending wall for supporting a body head with an opening disposed through said holder adjacent said wall, said wall tapering upwardly and outwardly from said opening and being curved for supporting a body head with an opening dispose through said holder adjacent said wall, said wall defining a tapering said wall on all portions of said side wall, and with said opening presenting a substantially conical configuration in one plane and in a plane transverse thereto defining an enlarged section for said opening and a tapering narrow section, an insert member composed of a resilient material having a head holder portion having substantially the same configuration as said head holder with an opening disposed through said insert member and complementary to said opening in said head holder, said insert member having a side wall for covering substantially all portions of said side wall of said head holder member, said curved wall being composed of a carbon fiber material and a connecting section extending from said wall.

7. The head holder member of claim 6 wherein said connecting section is defined by two spaced apart flanges.

8. The insert member of claim 6 wherein said member opening has a substantially tear drop configuration when viewed in a plane substantially transverse to said conical configuration.

* * * * *

UNITED STATES PATENT AND TRADEMARK OFFICE
CERTIFICATE OF CORRECTION

PATENT NO. : 5,233,713
DATED : August 10, 1993
INVENTOR(S) : Lawrence E. Murphy, et. al.

It is certified that error appears in the above-indentified patent and that said Letters Patent is hereby corrected as shown below:

```
Column 4, claim 5, line 51, after "holder" deice should be--devoce--.
         claim 5, line 52, before "panel" mountain should be --mounting--.
         claim 5, line 53, after "member" a should be deleted--.
         claim 6, line 62, after "opening" dispose should be --disposed--.
         claim 6, line 64, after "tapering" said should be --side--.
Column 6, claim 8, line 6, after 'said" --insert should be added--.
```

Signed and Sealed this

Fifth Day of April, 1994

Attest:

BRUCE LEHMAN

*Attesting Officer*   Commissioner of Patents and Trademarks

UNITED STATES PATENT AND TRADEMARK OFFICE
CERTIFICATE OF CORRECTION

PATENT NO. : 5,233,713
DATED : August 10, 1993
INVENTOR(S) : Lawrence E. Murphy et al.

It is certified that error appears in the above-identified patent and that said Letters Patent is hereby corrected as shown below:

Column 4, claim 5, line 51, after "holder" deice should be --device--.

claim 5, line 52, before "panel" "mountain" should be --mounting--.

claim 5, line 53, after "member" "a" should be deleted.

claim 6, line 62, after "opening" "dispose" should be --disposed--.

claim 6, line 64, after "tapering" "said" should be --side--.

Column 6, claim 8, line 6, after "said" --insert-- should be added.

This Certificate supersedes the Certificate of Correction issued April 5, 1994.

Signed and Sealed this

Seventh Day of June, 1994

Attest:

BRUCE LEHMAN

Attesting Officer  Commissioner of Patents and Trademarks